United States Patent
Sjostrom et al.

[11] Patent Number: 5,749,885
[45] Date of Patent: May 12, 1998

[54] SURGICAL INSTRUMENT WITH EMBEDDED CODING ELEMENT

[75] Inventors: Douglas D. Sjostrom, Reading, Mass.; Michael A. Fritschy, Derry; Peter M. Cesarini, Londonderry, both of N.H.; Alexander Grinberg, Newton; William G. McGee, Tyngsboro, both of Mass.; Graham Smith, Plaistow, N.H.

[73] Assignee: Smith & Nephew, Inc., Andover, Mass.

[21] Appl. No.: 538,298

[22] Filed: Oct. 2, 1995

[51] Int. Cl.⁶ .................................. A61B 17/32
[52] U.S. Cl. ..................... 606/170; 606/180; 604/22
[58] Field of Search ............... 606/79, 80, 167–172, 606/174–190; 604/22; 128/750–755

[56] References Cited

U.S. PATENT DOCUMENTS

| | | |
|---|---|---|
| Re. 34,556 | 3/1994 | Sjostrom et al. . |
| 3,143,900 | 8/1964 | Oeckl et al. . |
| 3,578,872 | 5/1971 | McBurnie . |
| 3,749,098 | 7/1973 | De Bennetot . |
| 3,817,237 | 6/1974 | Bolduc . |
| 3,835,858 | 9/1974 | Hagen . |
| 3,924,631 | 12/1975 | Mancusi, Jr. . |
| 3,990,452 | 11/1976 | Murry et al. . |
| 4,071,029 | 1/1978 | Richmond et al. . |
| 4,080,737 | 3/1978 | Fleer . |
| 4,209,273 | 6/1980 | Lehnen . |
| 4,274,407 | 6/1981 | Scarlett . |
| 4,289,131 | 9/1981 | Mueller . |
| 4,292,571 | 9/1981 | Cuneo . |
| 4,305,126 | 12/1981 | Beier et al. . |
| 4,413,936 | 11/1983 | Kuhlmann . |
| 4,424,030 | 1/1984 | Smiley et al. . |
| 4,496,342 | 1/1985 | Banko . |
| 4,504,227 | 3/1985 | Lohm . |
| 4,514,172 | 4/1985 | Behringer . |
| 4,515,564 | 5/1985 | Lohm . |
| 4,540,318 | 9/1985 | Hornung et al. . |
| 4,593,681 | 6/1986 | Soni . |
| 4,611,601 | 9/1986 | Bowman . |
| 4,673,318 | 6/1987 | Hornung et al. . |
| 4,705,038 | 11/1987 | Sjostrom et al. . |
| 4,737,214 | 4/1988 | Leurink et al. . |
| 4,817,607 | 4/1989 | Tatge . |
| 5,269,794 | 12/1993 | Rexroth . |

FOREIGN PATENT DOCUMENTS

| | | |
|---|---|---|
| 0010890 | 5/1980 | European Pat. Off. . |
| 0053646 | 6/1982 | European Pat. Off. . |
| 56-54827 | 5/1981 | Japan . |
| 57-45838 | 3/1982 | Japan . |
| 57-5208 | 6/1982 | Japan . |
| 57-93314 | 6/1982 | Japan . |
| 58-188445 | 11/1983 | Japan . |
| 58-188446 | 11/1983 | Japan . |
| 60-884 | 1/1985 | Japan . |
| 504265 | 10/1961 | Switzerland . |

(List continued on next page.)

OTHER PUBLICATIONS

"Arthroscopic Surgical System," Dyonics, Inc. (dated Feb. 1, 1993).
"Arthroplasty System," Dyonics, Inc., (dated Dec. 15, 1983).
"Intra–Articular Surgical II," Dyonics, Inc. (dated Dec. 15, 1983).
"Synovectomy System," Dyonics, Inc. (dated Feb. 1, 1984).

*Primary Examiner*—William Lewis
*Attorney, Agent, or Firm*—Fish & Richardson P.C.

[57] ABSTRACT

A surgical instrument includes a plastic hub which is received by a handpiece for operating the instrument. The plastic hub includes a wall that encloses a passage that receives a surgical tool-carrying member, and at least one detectable coding element is embedded at a selected circumferential position in the wall. For example, the coding element is embedded in a hole disposed in the wall. Alternatively, the coding element is molded into the wall during injection molding of the hub. The coding element is, for example, a magnet.

47 Claims, 8 Drawing Sheets

FOREIGN PATENT DOCUMENTS

| | | |
|---|---|---|
| 1032340 | 6/1966 | United Kingdom . |
| 1156291 | 6/1969 | United Kingdom . |
| 1156292 | 6/1969 | United Kingdom . |
| 1156293 | 6/1969 | United Kingdom . |
| 1156294 | 6/1969 | United Kingdom . |
| 1157667 | 7/1969 | United Kingdom . |
| 1158439 | 7/1969 | United Kingdom . |
| 1211271 | 11/1970 | United Kingdom . |
| 1268764 | 3/1972 | United Kingdom . |
| 1433912 | 5/1973 | United Kingdom . |
| 1441549 | 5/1974 | United Kingdom . |
| 1361497 | 7/1974 | United Kingdom . |
| 1414081 | 11/1975 | United Kingdom . |
| 1433911 | 4/1976 | United Kingdom . |
| 1394010 | 7/1976 | United Kingdom . |
| 1460046 | 12/1976 | United Kingdom . |
| 1504496 | 3/1978 | United Kingdom . |

5,749,885

SURGICAL INSTRUMENT WITH EMBEDDED CODING ELEMENT

BACKGROUND OF THE INVENTION

This invention relates to powered surgical instruments, such as for arthroscopy.

Powered arthroscopic surgical instruments typically include a stationary outer member and an inner member that is rotated within the outer member by a motorized handpiece. A surgical tool, such as a blade, bone abrading burr, or other suitable cutting implement, is supported on the distal end of the inner member and cuts tissue exposed to it through an opening in the distal end of the outer member. The proximal end of the outer member is mounted to a cylindrical, hollow hub which fits within the handpiece. The cylindrical hub wall encloses a passage that rotatably receives a drive shaft mounted on the proximal end of the inner member. The drive shaft is engaged by the motor when the hub is inserted into the handpiece. During operation, tissue fragments cut by the rotating surgical tool and irrigating fluid are withdrawn from the surgical site through the interior of the inner member and through a suction port in the drive shaft by a vacuum source connected to the handpiece.

In arthroscopic surgery, different types of instruments operate in different optimal speed ranges. For example, bone-abrading burrs operate at relatively high speeds, while shaver blades perform optimally at lower speeds. U.S. Pat. No. 4,705,038 (now Reissue Patent No. Re. 34,556), entitled "Surgical System for Powered Instruments," assigned to the present assignee and incorporated herein by reference (hereinafter referred to as the '038 patent), describes selectively coding such instruments with coding elements (e.g., magnets) according to the speed range within which the instrument is to operate. For example, a surgical instrument may be coded with zero, one, or two magnets. The magnets are "read" by a set of sensors (such as reed switches) selectively positioned in the handpiece to detect the magnetic fields of the magnets. A motor control unit connected to the handpiece detects the outputs of the sensors and responds by setting the motor to the speed range that corresponds to the instrument's code.

The instruments can be magnetically coded in several ways. For example, in the '038 patent the magnets are located either in adapters which connect the hub of the instrument to the handpiece, or in an integral unit made by merging the adapter and the hub. Alternatively, the magnets may be disposed in the hub itself, which may be made of plastic. For example, in U.S. Pat. No. 5,269,794 issued to Rexroth, the magnets are positioned in axially-extending, open-ended recesses in a first annular plastic section of the hub, and a second annular plastic hub section is secured to the first annular section to close the recesses and hold the magnets therein.

SUMMARY OF THE INVENTION

This invention features numerous ways of embedding a detectable coding element in the plastic hub of a surgical instrument.

In one general aspect of the invention, the coding element is embedded at a selected circumferential position in the wall of the plastic hub that encloses the passage in the hub through which the inner member of the instrument is received.

Preferred embodiments include the following features.

The coding element (which is preferably a magnet) is embedded in a hole formed in the hub wall. The hole may be oriented radially or axially with respect to the longitudinal axis of hub.

Several techniques for embedding the coding element are contemplated. For example, the coding element can be embedded in the hole by a friction fit with the sides of the hole. The hole sides may include protrusions that are deformed when the coding element is installed in the hole to assist in the friction fit.

The coding element can be embedded by displacing a region of the plastic wall adjacent to the hole to lie over at least a portion of the coding element. The displaced region of plastic may completely cover the coding element, or not. In the latter case, the displaced region of plastic can define a pair of flaps each of which at least partially covers the coding element.

The coding element can be embedded in the hole by securing a plastic cap over the coding element. The hole and the plastic cap are configured so that the cap is flush with the exterior surface of the hub wall adjacent to the hole.

Adhesive may be used to embed the coding element in the hole. If the coding element is recessed in the hole from the hub's exterior surface, the adhesive can be used to fill the recess.

Another approach for embedding the coding element is to mold the coding element into the hub wall during injection molding of the hub itself. The coding element is held in its selected circumferential position during at least part of the injection molding process. In one embodiment, the coding element is held in place until injection molding is complete, and then is withdrawn. Alternatively, the coding element is held in place until part of the coding element has been covered by plastic, and then the coding element is released and the injection molding completed. The latter technique is particularly useful if the molded wall of the hub is to completely surround the coding element.

The hub is constructed so that up to a selected number of coding elements corresponding to a selected number of circumferential positions can be embedded in the hub wall. For example, a plurality of holes—each one of which can, but need not, contain a coding element—are disposed at the selected circumferential positions in the wall. Any number of coding combinations are possible. For example, all, or less than all, of the holes may contain a coding element. Alternately, of course, the coding elements can be molded into the hub at some or all of the selected circumferential hub positions. The number of coding elements provided for a given surgical instrument, and their relative positions around the circumference of the hub, determines the "code" of that instrument.

The hub also supports a seal, which helps avoid vacuum leakage between the hub and a handpiece during operation. In one embodiment, the seal is disposed on a transverse surface of the hub at the proximal end of the hub. In hub configurations in which the coding elements are embedded in axial holes, the holes may be disposed in the transverse surface, and may be covered by the seal. Alternatively, the seal includes at least one window that exposes a hole. In another embodiment, the seal is located elsewhere on the hub, remote from the transverse surface.

Another aspect of the invention features a surgical system that includes the surgical instrument and a handpiece adapted to receive the hub of the instrument in a selected orientation with respect to the selected circumferential position of the coding element. The handpiece is adapted to move the inner member within the outer member to cause the surgical tool to cut tissue admitted through the opening in the outer member. At least one sensor is positioned in the handpiece for detecting whether the coding element is present in the hub.

Preferred embodiments include the following features.

The coding element includes a magnet. In one embodiment, the sensor is a switch adapted to be closed by the magnetic field generated by the magnet. As a result, each selected circumferential position of the hub represents one of two possible coding states—magnet absent and magnet present. In another embodiment, the sensor is a device that can also determine the orientation of the magnetic field. This allows each hub position to also represent coding states corresponding to different magnetic field orientations.

The handpiece includes a motor for rotating the inner member within the outer member. A controller responds to the detection provided by the sensor by adjusting an operating parameter of the motor. For example, the controller adjusts the motor speed range according to the "code" detected by the sensor.

Embedding the magnets in the wall of the hub itself allows the magnets to be positioned closely to the exterior surface of the hub, thereby reducing the spacing between the magnets and sensors. This reduces the magnets' required magnetic field strength, and leads to a more economical design. At least in some embodiments, the magnets are accessible for cleaning and/or replacement, if desired. Some embodiments also carry the additional advantage of eliminating components that were previously used to help capture the magnets in the hub.

Other features and advantages will become apparent from the following detailed description, and from the claims.

DESCRIPTION OF THE PREFERRED EMBODIMENT

Figure 1:
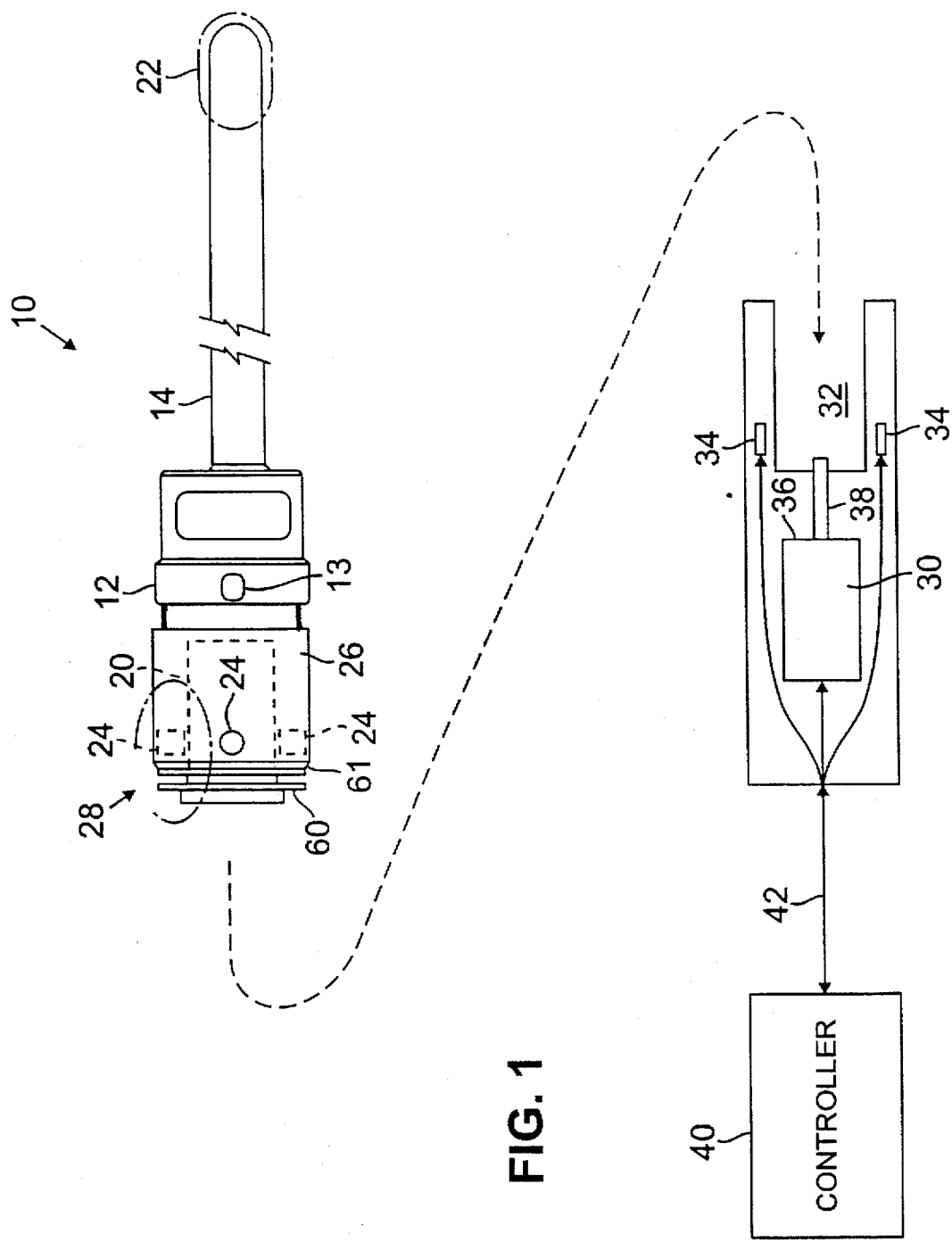
FIG. 1 shows a surgical instrument with embedded magnets and a handpiece.

Referring to FIG. 1, surgical instrument 10 includes a cylindrical plastic hub 12 to which the proximal end of an elongated outer tube 14 is mounted. An elongated inner tube 16 is disposed for rotation within outer tube 14 (tubes 14, 16 typically are metal). A plastic drive shaft 18 is mounted to the proximal end of inner tube 16 and is rotatably received within a passage 20 in hub 12. At the distal end 22 of instrument 10 (shown schematically in FIG. 1) a cutting implement (such as a blade or burr) carried at the distal end of inner tube 16 cuts tissue exposed thereto by an opening in outer tube 14 (the opening is, for example, a side-facing window or an open end of tube 14).

Up to four magnets 24 (three of which are shown in FIG. 1) are embedded within the cylindrical wall 26 of plastic hub 12 that encloses passage 20, near the proximal end 28 of hub 12. Magnets 24 serve as coding elements that identify the type of surgical instrument to a motorized handpiece 30 that operates instrument 10, as described below. Magnets 24 are located at selective positions around the circumference of hub 12 so that, when hub 12 is installed into a cylindrical chamber 32 in handpiece 30, magnets 24 are positioned adjacent to a set of sensors 34 mounted in the walls of handpiece 30. (only two sensors 34 are shown in FIG. 1, but it will be appreciated that, because instrument 10 can contain up to four magnets, four sensors 34 are disposed around the periphery of chamber 32.)

Sensors 34 can be any suitable devices for detecting the presence (or absence) of magnets 24. For example, sensors 34 may be Hall effect devices, which in addition to detecting whether a magnet 24 is present can also determine the orientation of the magnetic field produced by magnet 24. Alternatively, sensors 34 may be reed switches.

Handpiece 30 includes a motor 36 the drive shaft 38 of which rotatably engages instrument drive shaft 18 when surgical instrument 10 is inserted in chamber 32. Motor 36 is controlled by a controller 40, which is connected by a cable 42 to handpiece 30. Cable 42 also carries signals from sensors 34 to controller 40 for processing. One example of controller 40 is discussed in the '038 patent.

Figure 2:
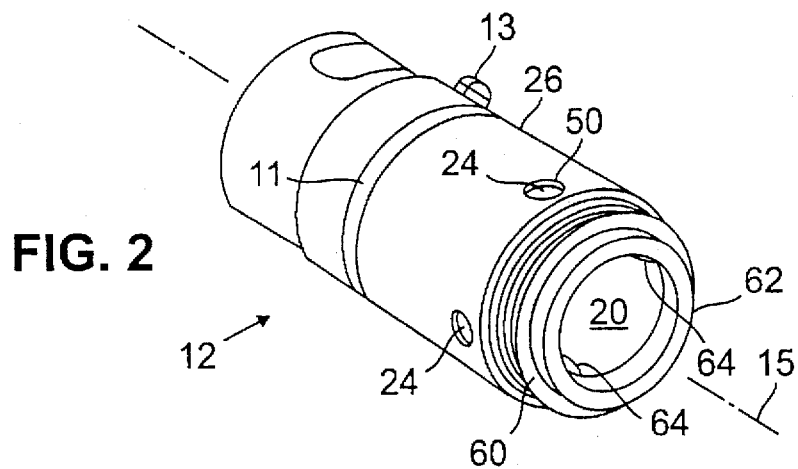
FIG. 2 is a perspective view of the hub of the surgical instrument of FIG. 1.
Figure 3:
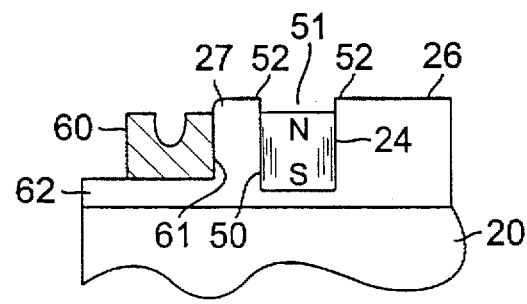
FIG. 3 illustrates one technique for embedding a magnet in the hub of the surgical instrument of FIG. 1.

Referring to FIGS. 2 and 3, hub 12 and the configuration of embedded magnets 24 are shown in more detail. Hub 12 is a one-piece plastic, cylindrical member formed by injection molding. One or more holes 50, each of which can contain one magnet, are formed are radially (relative to the longitudinal axis 15 of hub 12) in the plastic cylindrical wall 26 of hub 12. Radially-extending holes 50 are located at selected positions around the circumference of hub 12 relative to a plastic locator stub 13 formed on the outer surface of hub 12 during injection molding. Holes 24 can be either be formed during the injection molding process or thereafter (such as by drilling). In either case, cylindrical wall 26 is sufficiently thick relative to the size magnets 24 to securely embed magnets 24 therein. For example, the thickness of wall 26 may be such that 0.035–0.040 inches or less of plastic, or 0.065–0.070 inches or more of plastic, are present on each radial side of magnet 24 (which has a dimension in the radial direction of, e.g., between 0.065–0.100 inches). Of course, magnets 24 need not be radially centered within wall 26. Holes 50 are spaced from passage 20 by a portion of wall 26 to isolate magnets 24 from fluids and tissue fragments withdrawn through inner tube 16 (but holes 50 may intersect passage 20, if desired).

Each magnet 24 is a small cylinder, the diameter of which closely approximates that of hole 50. Magnet 24 is installed radially so that its cylindrical sides are press-fit into hole 50. As a result, the flat faces of magnet 24 (and hence the "north" (N) and "south" (S) poles of magnet 24) are arranged radially, rather than circumferentially around hub 12. If reed switches are used as sensors 34, the relative orientations of the north and south magnet poles in hole 50 are unimportant. But if Hall effect devices (which detect the orientation of the magnetic field as well as the presence or absence of a magnet 24) are used, the orientation of magnet 24 in hole 50 provides an additional coding indication and thus must be selected accordingly.

The friction fit with the sidewalls of hole 50 suffices to embed magnet 24 in place within cylindrical wall 26. But to provide additional security, one or more regions 52 of the sidewalls of hole 50 are displaced or "staked" over magnet 24. "Staking" involves heating the plastic sidewalls sufficiently to melt sidewall regions 52, while simultaneously urging regions 52 downwardly against the flat upper surface of magnet 24.

A ring-shaped silicone seal 60 is installed on a transverse annular surface 61 at hub proximal end 28, and is axially spaced from magnet-containing holes 24 by an integral flange 27 of hub cylindrical wall 26. Seal 60 surrounds a collar 62 molded integrally at the proximal end of hub 12, and is held in place by a pair of tabs 64 (FIG. 3) that extend into corresponding openings in collar 62. Seal 60 provides a vacuum-tight fit between hub 12 and handpiece 30, which prevents leakage of suction applied (by means not shown) to the surgical site through the instrument to aspirate fluids and tissue. In addition, tabs 62 engage inner tube drive shaft 18 to help prevent inner tube 16 from sliding out of hub 12 (tabs 62 can be overcome manually by pulling inner tube 16 proximally out of hub 12).

Referring again to FIG. 1, the operation of the system is as follows. When an instrument 10 is inserted into handpiece 30, stub 13 ensures that hub 12 is oriented within chamber 32 so that any magnets 24 carried by hub 12 are positioned adjacent to sensors 34. Each sensor 34 detects whether a magnet 24 is present and communicates this information to controller 40 via cable 42. For example, if sensors 34 are reed switches, those reed switches positioned adjacent to a magnet 24 are closed by the magnet's magnetic field, while the other reed switches remain in the "open" state. Thus, each magnet position in hub 12 can have one of two coding states—magnet present and magnet absent. The position of each reed switch, and hence the "code" for the particular instrument 10, is determined by controller 40.

If sensors 34 are Hall effect devices, they additionally detect the orientation of the magnetic field produced by each magnet 24 in hub 12. Put another way, when Hall effect devices are used as sensors 34, each magnet position in hub 12 can have any of three coding states—magnet absent, magnet present with north (N) pole facing radially outwardly (as shown in FIG. 3), and magnet present with south (S) pole facing radially outwardly. The state of each Hall effect sensor (and hence the "code" for the particular instrument 10) is determined by controller 40.

Thus, it will be appreciated that wide variety of instrument codes are possible. As a result, a manufacturer can subdivide a host of surgical instruments 10 into a correspondingly large number of different "types," each of which is uniquely coded by embedded magnets 24. Controller 40 is programmed to associate each possible instrument code (and thus, each type of instrument 10) with a set of operating conditions that are optimal for that type of instrument. For example, controller 40 can set the operating speed range of motor 30, the maximum torque provided by motor 30, and any other parameter of motor 30, all based on the instrument's code. In addition, controller 40 can adjust other operating parameters based on the code provided by embedded magnets 24. Examples include the maximum torque applied by motor 30, the permitted modes of operation of motor 30 (e.g., whether motor 30 is permitted to operate in the reverse directions or to oscillate between the forward and reverse directions), and the operation of peripheral components (such as the vacuum devices used to aspirate irrigation fluids and tissue from the surgical site).

Other embodiments are within the scope of the following claims.

For example, magnets 24 can be embedded within holes 50 in other ways. As mentioned above, the magnets may simply be embedded in place by friction. Adhesive (for example, a heat or ultraviolet-light curing epoxy may be used instead of (or in addition to) staking.

Figure 3A:
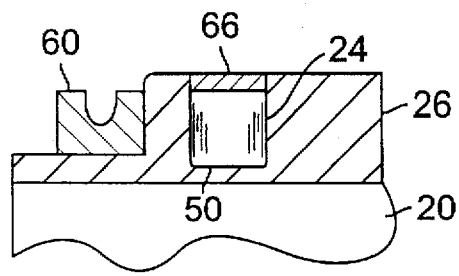
FIGS. 3A–3D show alternative ways of embedding the magnet in the hub.

Referring to FIG. 3A, yet another embedding option is to cover each magnet 24 with a round plastic cap 66. Cap 66 may be glued or staked in place and preferably fills the small indent 51 (FIG. 3) between the upper surface of magnet 24 and the exterior surface of hub wall 26. Plastic caps 66 will prevent liquid and particles from accumulating on the upper surfaces of magnets 24, in addition to providing a pleasing appearance (e.g., caps 66 and hub 12 may be made from the same color plastic). As an alternative, the upper surface (or all surfaces) of magnets 24 may be coated with plastic.

Figure 3B:
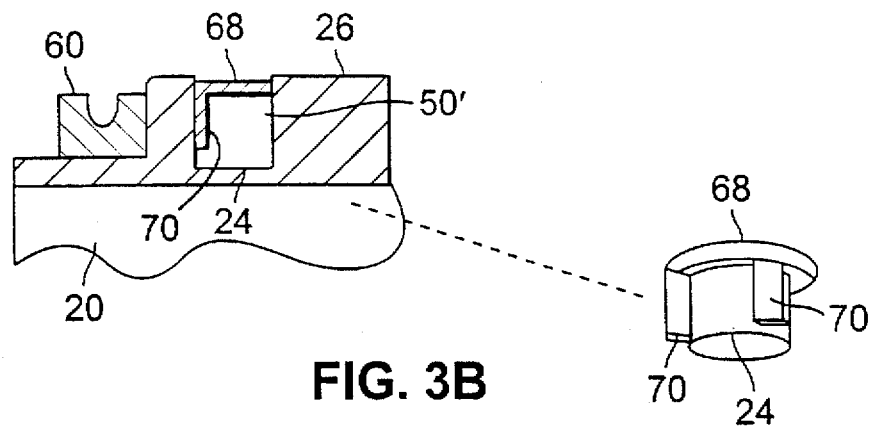

Referring to FIG. 3B, an alternative plastic cap 68 is larger in diameter than magnet 24 and includes a set of (e.g., three or four) legs 70 arranged around the circumference of magnet 24 and extending along the sides of magnet 24. Hole 50' is larger than magnet 24 to accommodate legs 70, which may extend the full depth of hole 50' or (as shown) terminate above the base of hole 50'. Legs 70 are secured to the sides of hole 50' by a friction fit, gluing, or staking.

During manufacturing, a large number of legged caps 68 may be fabricated as a strip of interconnected caps 68, each of which is filled with a magnet 24. The magnet-containing caps 68 can be emplaced in hubs by an automated process, thereby simplifying and speeding the fabrication process. Rather than having a discrete set of legs, cap 68 may instead include a cylindrical sleeve that fully surrounds magnet 24.

The small indent 51 between the upper surface of magnet 24 and the exterior of hub cylindrical wall 26 may be reduced from that shown in FIG. 3 or may be eliminated altogether (e.g., by reducing the depth of holes 50 so that magnets 24 are essentially "flush" with the exterior surface of hub wall 26. This will help ensure that indents 51 do not interfere with the operation of mechanical "ball locks" in handpiece 30. (A ball lock is a spring-mounted ball bearing that extends into hub-receiving chamber 32 for securing hub 12 within handpiece 30 during operation. The user retracts the balls (by a mechanism not shown) when installing hub 12 into and removing hub 12 from handpiece 30. When instrument 10 is fully inserted, the balls extend into a circumferential groove 11 in hub 12 (FIG. 2) to latch hub 12 in place in the handpiece.)

Figure 3C:
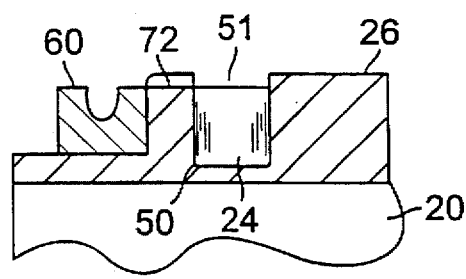
Figure 3D:
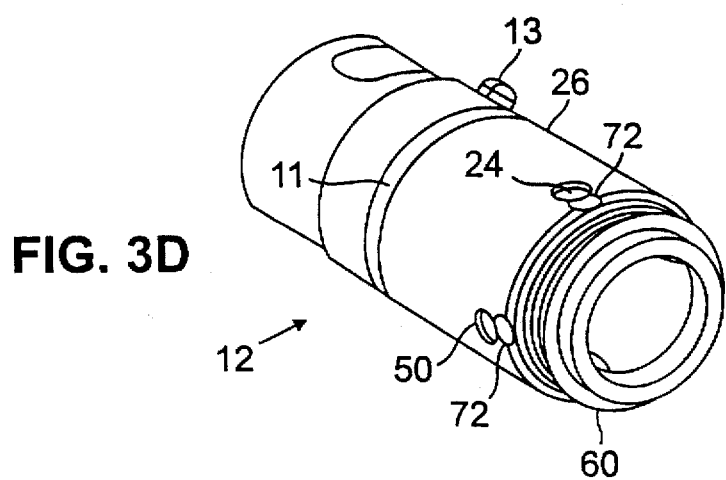
Figure 4:
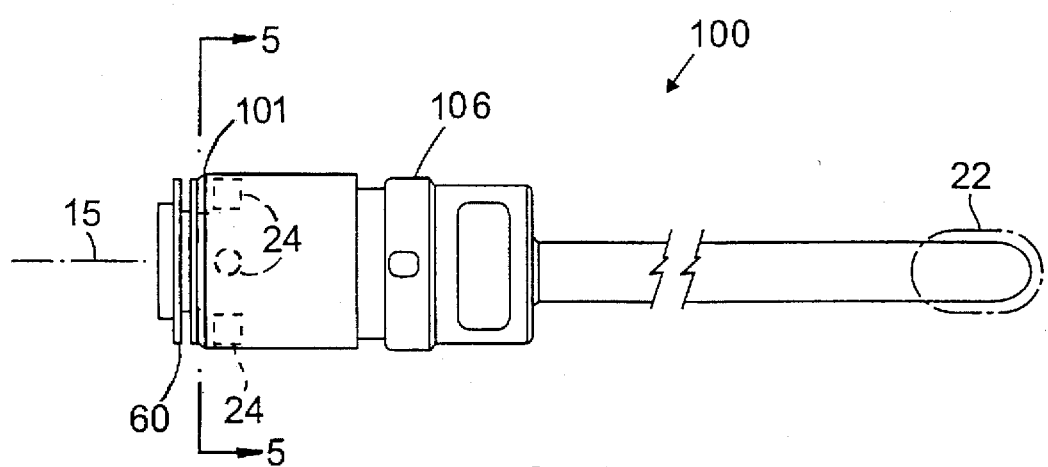
FIGS. 4–11 illustrate several other alternative techniques for embedding a magnet in a surgical instrument hub.

Referring to FIGS. 3C and 3D, small grooves 72 may be provided in the exterior surface of hub wall 26 adjacent to holes 50. Grooves 72 will allow the ball locks to smoothly bypass holes 50.

Magnets 24 may be embedded in hub cylindrical walls 26 in still other ways. For example, referring to FIGS. 4–7 in instrument 100, magnet-containing holes 102 are disposed axially along axis 15 of hub 106 (rather than radially). Magnets 24 are installed in axially-extending holes 102 in the cylindrical walls 104 of one-piece plastic hub 106. (The inner tube and drive shaft of instrument 100 are not shown.)

Figure 5:
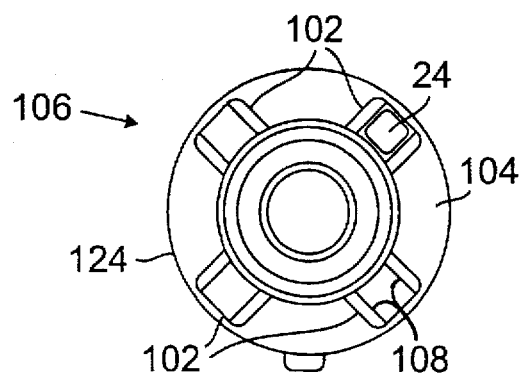
Figure 6:
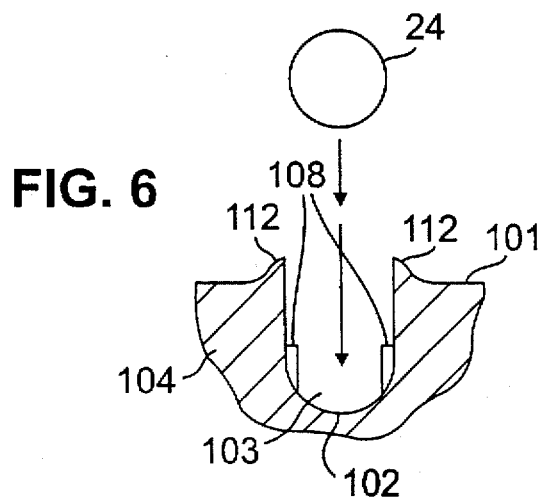

Holes 102 are open at an annular surface 101 of cylindrical wall 104 near the proximal end of hub 106 to allow magnets 24 to be inserted in the axial direction (one magnet 24 is shown in FIG. 5). Each hole 102 includes a lower chamber 103 that is slightly wider than the diameter of magnet 24. A set of integral crush ribs 108 are formed during molding and protrude into chamber 103 from opposite sides thereof (FIG. 6). The spacing between opposing crush ribs 108 is less than the diameter of magnet 24. Thus, when magnet 24 is inserted into hole 102 (as shown by the arrow in FIG. 6), the cylindrical sides of magnet 24 engage and deform crush ribs 108. Deformed crush ribs 108 securely embed magnet 24 in hole 102.

Figure 7:
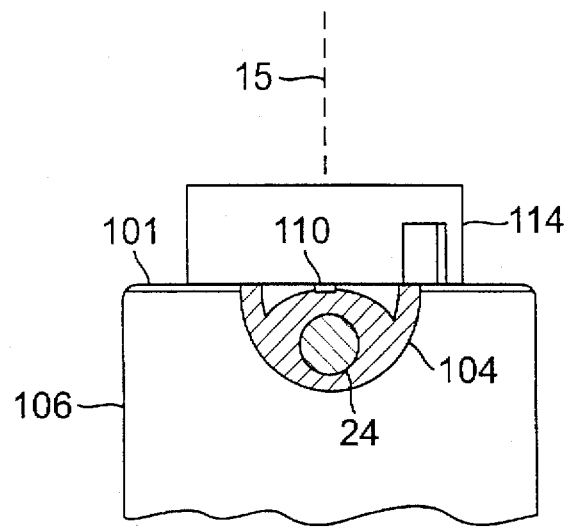

Nevertheless, to further embed magnets 24 each magnet-containing hole 102 is also closed during fabrication by forming an integral plastic shell 110 over magnet 24 (FIG. 7). Shell 110 is formed by melting regions of the sidewalls of hole 102 and urging the melted plastic together over magnet 24 to completely cover magnet 24 and close hole 102—fully encapsulating magnet 24 within hub 106.

Each shell 110 is formed as follows. A pair of ridges 112 (FIG. 6) are molded into hub annular surface 101 adjacent the sides of each hole 102. After magnet 24 has been inserted into lower chamber 103, an ultrasonic horn (not shown) is placed over hole 102 so that the edges of the horn engage ridges 112. The horn is then activated with high frequency energy, which causes the horn to vibrate rapidly and melt ridges 112 and underlying regions of the hole sidewalls. Simultaneously, the horn is pressed downwardly to displace the melted plastic into hole 102. Magnet 24 supports the melted plastic so that the plastic flows over and around the magnet, thereby forming shell 110.

Ridges 112 and the sidewalls of hole 102 provide sufficient material to ensure that the melted plastic completely covers magnet 24, extending the full length and width of hole 102. When the horn is de-energized and removed, melted plastic shell 110 solidifies over and around magnet 24, thereby closing hole 102 and encapsulating magnet 24 therein. Put another way, magnet-containing hole 102 is closed and magnet 24 is ultrasonically welded in place within single-piece plastic hub 106 using regions of hub 106 that previously formed the sidewalls (and ridges 112) of hole 102.

Plastic shells 110 may be formed one at a time (using a single ultrasonic horn), or all shells 110 may be formed simultaneously using a set of four ultrasonic horns. In either case, after all plastic shells 110 are formed, silicone seal 60 (discussed above and shown in FIG. 4) is secured over annular hub surface 101 around hub collar 114 as discussed above (one opening in collar 60 for a seal tab 62 is shown in FIG. 7).

Figure 8:
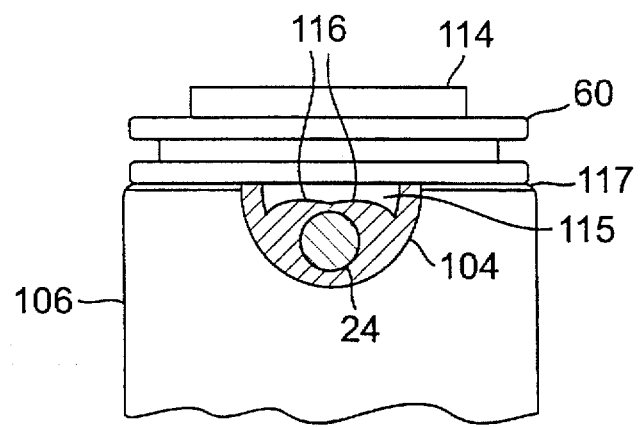

Referring to FIG. 8, magnets 24 need not be fully encapsulated by plastic of hub walls 104. Instead, a reduced amount of plastic from the sides of each hole 102 may be melted (such as by the ultrasonically welding technique discussed above) to form a pair of plastic flaps 116 over magnet 24. Flaps 116 conform to the shape of, and almost completely cover, magnet 24, as shown. Because a reduced amount of plastic is needed to form flaps 116 relative to that required to fabricate shells 110, ridges 112 (FIG. 6) need not be provided adjacent to holes 102. In fact, if desired, a pair of notches may be formed in hub surface 101 adjacent each hole 102 to receive and help properly align the ultrasonic horn over the hole.

Figure 9:
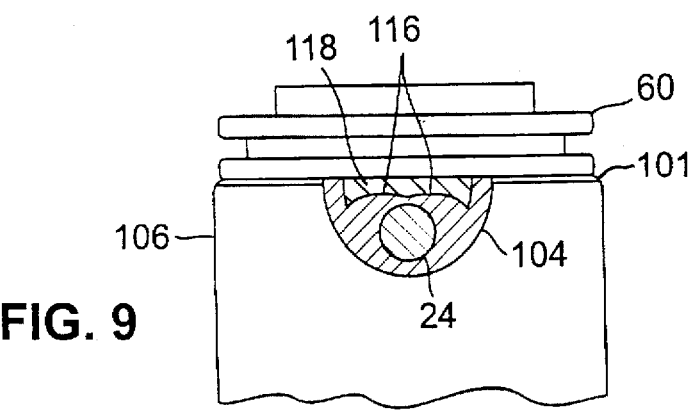

Referring also to FIG. 9, the region 115 between flaps 116 and the annular hub surface 101 may be filled with a potting material 118 to fully encapsulate magnet 24. Any suitable potting material 118 (for example, an ultraviolet curing adhesive) can be used. Potting material 118 should be sufficiently rugged to withstand sterilization procedures such as autoclaving. Potting material 118 may, of course, also be used with plastic shells 110 of FIG. 7.

Figure 10:
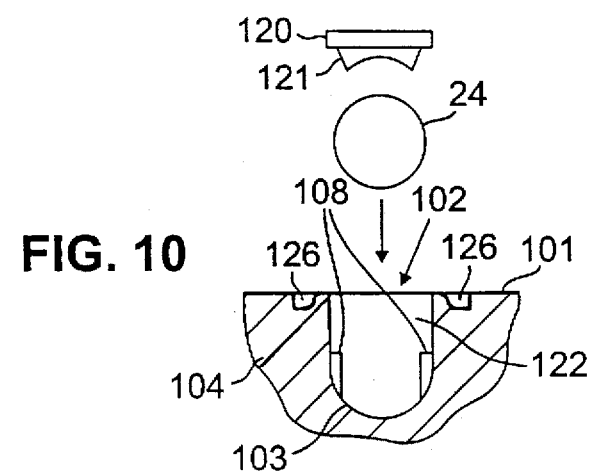
Figure 11:
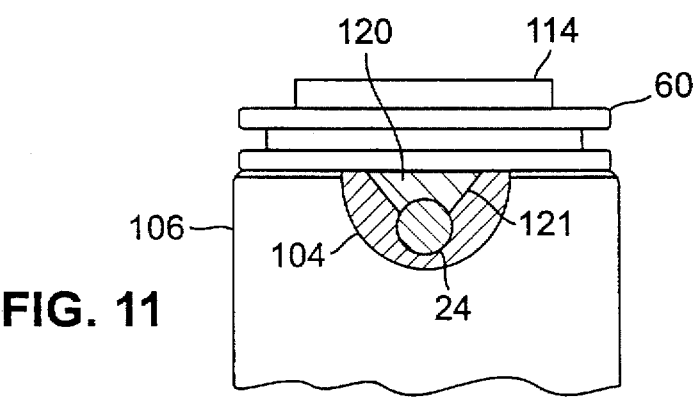

FIGS. 10 and 11 illustrate yet another way of embedding magnets 24 within cylindrical walls 104 of hub 106. Instead of using integral regions of hub walls 104, a small plastic cap 120 is secured in place over each magnet 24 to encapsulate it within hole 102. Cap 120 is rectangular and fits within a corresponding enlarged recess 122 in the upper region of hole 102. This allows cap 120 to lie flush with the hub surface 101 (FIG. 11). Alternatively, recess 122 may be omitted, and cap 120 may rest on surface 101. The edges of each cap 120 may be curved (rather than straight) so that caps 120 generally follow the curved contour of cylindrical hub wall 104.

The underside 121 of cap 120 is arched to match the cylindrical sides of magnet 24. Cap 120 is secured in place by the ultrasonic welding technique discussed above. A pair of ridges 126 formed in the upper surface of recess 122 adjacent hole 102 serve as energy directors to focus the energy applied by the ultrasonic horn and cause the sidewalls of hole 102 to melt and bond with cap underside 121 over magnet 24 as cap 120 is urged downwardly. As a result, cap 120 fully encapsulates magnet 24 within hub wall 104, as shown in FIG. 11.

Figure 12:
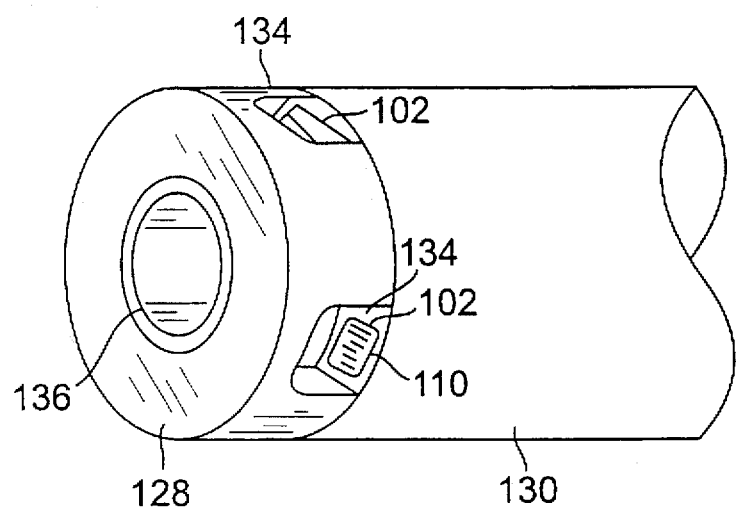
FIGS. 12 and 13 show alternative arrangements of a seal on the surgical instrument hub.
Figure 13:
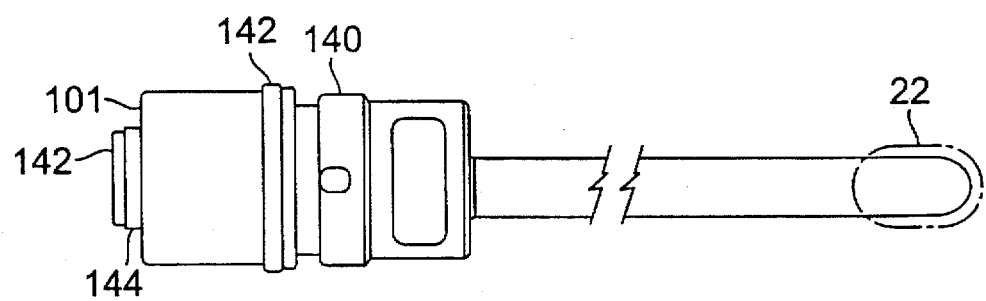

Referring to FIGS. 12 and 13 seal 60 may have other configurations, and may be located elsewhere on the instrument. For example, seal 128 used with hub 130 of FIG. 12 includes a set of windows 134 that expose magnet-containing holes 102. In FIG. 12, plastic shells 110 (FIG. 7) cover magnets 24 in holes 102. But any of the other techniques described above for axially retaining magnets in holes 102 may be used instead. Seal 128 is affixed to hub collar 136 in the same way as discussed above for seal 60.

As shown in FIG. 13, the seal can be placed remotely from hub surface 101 and the proximal end of the hub. In hub 140, the sealing function is provided by an O-ring 142, located intermediate annular surface 101 (i.e., the surface of the hub walls in which the magnet-containing holes are formed) and the hub distal end. Drive shaft retaining tabs 62 (FIG. 2) are held within openings (not shown) of hub collar 142 by a thin-walled sleeve 144 that does not cover magnet-containing holes 102. As a result, magnet-containing holes 102, whether covered by shells 110 (FIG. 7), flaps 116 (FIG. 8), potting material (FIG. 9), or caps 120 (FIG. 11), are visible.

Figure 14:
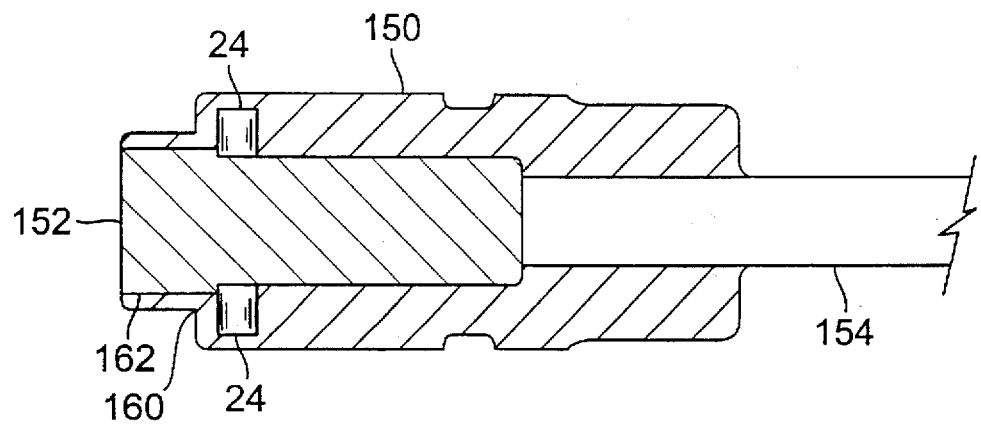
FIGS. 14–16 illustrate molding a magnet into a wall of a surgical instrument hub.
Figure 15:
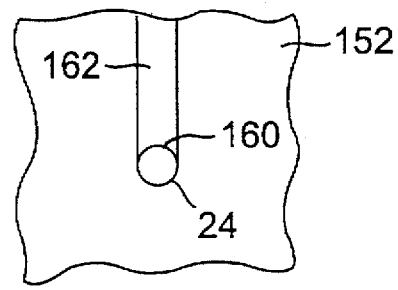
Figure 16:
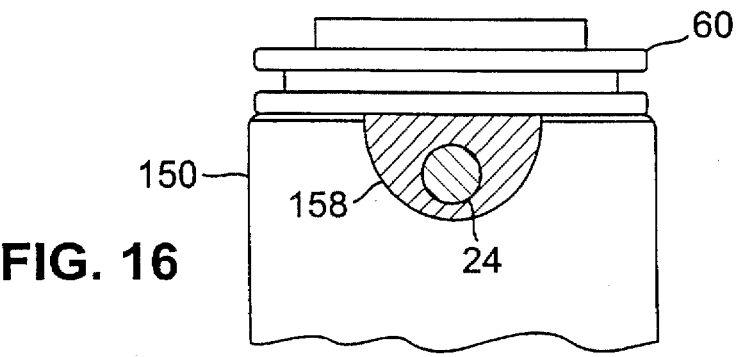

Referring to FIGS. 14-16, magnets 24 may be embedded within hub 150 during the injection molding process used to form hub 150. Each magnet 24 is held within a mold (not separately shown) for the hub by a core pin 152 that extends into the mold adjacent to a tube 154 that defines the interior surface of hub wall 158. Each magnet 24 is held within a corresponding cup-shaped seat 160 on a region 162 of core pin 152 in any suitable way (for example, pneumatically, mechanically, or magnetically).

Hub 150 may be formed in a single injection molding step. In this case, magnets 24 are held by core pin 152 (and core pin 152 remains in the mold) during the entire molding process. As a result, one circular face of each embedded magnet 24 is exposed to passage 20 (FIG. 1) in the hub that receives the inner tube drive shaft. In addition, regions 162 of core pin 152 create shallow slots along the inner surface of the cylindrical hub wall 158. Neither the exposed magnet face nor the slots interferes with the rotation of the drive shaft.

As an alternative, hub 150 may be injection molded in two steps. Part of magnet 24 is covered by plastic of cylindrical hub wall 158 in the first step, thereby securing magnet 24 in place. Then, magnets 24 are released by removing core pin 152, and replacing it with an element (not shown) slightly smaller in diameter. This provides space in the mold adjacent to magnets 24 for the subsequently-injected plastic. Then, remainder of hub 150 is formed in the second injection, thereby completely encasing magnet 24 in the plastic cylindrical walls 158 of hub 150 (i.e., no part of magnet 24 is visible).

The surgical instruments described herein typically are "disposable;" that is, the instruments are meant to be used once and then discarded. The surgical instruments may instead be "reusable" multiple times. In this case, the plastic hub and the techniques used to embed magnets 24 within the cylindrical walls of the hub must be sufficiently rugged to withstand sterilization after use.

Still other embodiments are within the scope of the claims.

What is claimed is:

1. A surgical instrument comprising
   a hollow outer member having an opening in a distal region thereof for admitting tissue,
   an inner member disposed for movement within said outer member, a distal region of said inner member supporting a surgical tool adjacent to said opening,
   a plastic hub mounted to a proximal region of said outer member and including a passage therethrough for receiving a proximal region of said inner member, said plastic hub including a wall that encloses said passage and includes a hole oriented radially with respect to a longitudinal axis of the hub, and
   at least one detectable coding element embedded in said hole of said wall.

2. The surgical instrument of claim 1 wherein said coding element is embedded in said hole by a friction fit with sides of said hole.

3. The surgical instrument of claim 2 wherein at least a portion of said sides of said hole includes protrusions adapted to be deformed when said coding element is received in said hole, thereby to provide said friction fit.

4. The surgical instrument of claim 1 wherein said coding element is embedded in said hole by a region of said plastic wall adjacent said hole that has been displaced to lie over at least a portion of said coding element.

5. The surgical instrument of claim 4 wherein said region of said plastic wall completely covers said coding element.

6. The surgical instrument of claim 4 wherein said region of said plastic wall includes a pair of flaps each of which at least partially covers said coding element.

7. The surgical instrument of claim 1 wherein said coding element is embedded in said hole by a plastic cap secured over said coding element.

8. The surgical instrument of claim 7 wherein said hole and said plastic cap are configured so that said cap is flush with an exterior surface of said wall adjacent to said hole.

9. The surgical instrument of claim 1 wherein said coding element is embedded in said hole by an adhesive.

10. The surgical instrument of claim 9 wherein said coding element is recessed in said hole from an exterior surface of said wall, said adhesive being disposed to fill said recess.

11. The surgical instrument of claim 1 wherein said wall completely surrounds said coding element.

12. The surgical instrument of claim 1 wherein said coding element includes a magnet.

13. The surgical instrument of claim 1 wherein said hub is constructed so that up to a selected number of coding elements corresponding to a selected number of circumferential positions can be embedded in said wall.

14. The surgical instrument of claim 13 wherein each one of said selected number of coding elements is embedded in a hole at one of said selected circumferential positions in said wall, and wherein said hole is oriented radially with respect to a longitudinal axis of said hub.

15. The surgical instrument of claim 13 further comprising a plurality of said holes disposed in said selected circumferential positions in said wall, each one of said holes being adapted to have a coding element embedded therein, and wherein each one of said holes is oriented radially with respect to a longitudinal axis of said hub.

16. The surgical instrument of claim 15 wherein a said coding element is embedded in at least one of said holes.

17. The surgical instrument of claim 15 wherein a said coding element is embedded in each one of said holes.

18. The surgical instrument of claim 15 wherein at least one of said holes does not have a said coding element embedded therein.

19. A surgical instrument comprising
   a hollow outer member having an opening in a distal region thereof for admitting tissue,
   an inner member disposed for movement within said outer member, a distal region of said inner member supporting a surgical tool adjacent to said opening,
   a plastic hub mounted to a proximal region of said outer member and including a passage therethrough for receiving a proximal region of said inner member, said plastic hub including a wall that encloses said passage, and
   at least one detectable coding element molded into said wall at a selected circumferential position in said wall.

20. A surgical instrument comprising
   a hollow outer member having an opening in a distal region thereof for admitting tissue,
   an inner member disposed for movement within said outer member, a distal region of said inner member supporting a surgical tool adjacent to said opening,
   a plastic hub mounted to a proximal region of said outer member and including a passage therethrough for receiving a proximal region of said inner member, said plastic hub including a wall that encloses said passage, and
   detectable coding elements molded into said wall at circumferential positions in said wall.

21. The surgical instrument of claim 20 wherein said coding elements are molded into said wall at all of said selected circumferential positions.

22. A surgical instrument comprising
   a hollow outer member having an opening in a distal region thereof for admitting tissue,
   an inner member disposed for movement within said outer member, a distal region of said inner member supporting a surgical tool adjacent to said opening,
   a plastic hub mounted to a proximal region of said outer member and including a passage therethrough for receiving a proximal region of said inner member, said plastic hub including a wall that encloses said passage, and
   at least one detectable coding element embedded at a selected circumferential position in said wall;
   wherein said wall terminates in a surface transverse to a longitudinal axis of said hub at a proximal end of said hub, said hub further comprising at least one axially-oriented hole at said transverse surface, said at least one coding element being embedded in said hole, and a seal mounted on said hub, wherein said seal is disposed on at least a portion of said transverse surface and covers said hole.

23. The surgical instrument of claim 22 wherein said seal includes at least one window that exposes said hole.

24. A surgical instrument comprising
   a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage, and at least one detectable coding element embedded at a selected circumferential position in said wall;

wherein said wall terminates in a surface transverse to a longitudinal axis of said hub at a proximal end of said hub, said hub further comprising at least one axially-oriented hole at said transverse surface, said at least one coding element being embedded in said hole, and a seal mounted on said hub, wherein said seal is disposed remote to said transverse surface.

25. A surgical system comprising a surgical instrument that includes a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage and includes a hole oriented radially with respect to a longitudinal axis of the hub, and at least one detectable coding element embedded in said hole of said wall; and a handpiece adapted to receive said hub in a selected orientation with respect to said selected circumferential position of said coding element, said handpiece being adapted to move said inner member within said outer member to cause said surgical tool to cut tissue admitted through said opening in said outer member, and at least one sensor positioned in said handpiece to detect whether said at least one coding element is present in said hub.

26. The surgical system of claim 25 wherein said at least one coding element includes a magnet, said at least one sensor comprising a switch adapted to be closed by a magnetic field generated by said magnet.

27. The surgical instrument of claim 25 wherein said at least one coding element includes a magnet, said at least one sensor comprising a device adapted to detect a magnetic field generated by said magnet and determine an orientation of said magnetic field.

28. The surgical system of claim 25 wherein said handpiece includes a motor for rotating said inner member within said outer member, and further comprising a controller for adjusting an operating parameter of said motor in response to said detecting by said at least one sensor.

29. A surgical instrument comprising a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage, and at least one detectable coding element embedded at a selected circumferential position in said wall;

wherein said wall includes at least one hole for receiving said at least one coding element, said at least one coding element being embedded in said hole by a friction fit with sides of said hole, and wherein at least a portion of said sides of said hole includes protrusions adapted to be deformed when said coding element is received in said hole, thereby to provide said friction fit.

30. A surgical instrument comprising a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage, and at least one detectable coding element embedded at a selected circumferential position in said wall;

wherein said wall includes at least one hole for receiving said at least one coding element, said at least one coding element being embedded in said hole by a region of said plastic wall adjacent said hole that has been displaced to lie over at least a portion of said coding element, and wherein said region of said plastic wall completely covers said coding element.

31. A surgical instrument comprising a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage, and at least one detectable coding element embedded at a selected circumferential position in said wall;

wherein said wall includes at least one hole for receiving said at least one coding element, said at least one coding element being embedded in said hole by a region of said plastic wall adjacent said hole that has been displaced to lie over at least a portion of said coding element, and wherein said region of said plastic wall includes a pair of flaps each of which at least partially covers said coding element.

32. A surgical instrument comprising a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage, and at least one detectable coding element embedded at a selected circumferential position in said wall;

wherein said wall includes at least one hole for receiving said at least one coding element, said at least one coding element being embedded in said hole by a plastic cap secured over said coding element, and wherein said hole and said plastic cap are configured so that said cap is flush with an exterior surface of said wall adjacent to said hole.

33. A surgical instrument comprising a hollow outer member having an opening in a distal region thereof for admitting tissue, an inner member disposed for movement within said outer member, a distal region of said inner member supporting a surgical tool adjacent to said opening, a plastic hub mounted to a proximal region of said outer member and including a passage therethrough for receiving a proximal region of said inner member, said plastic hub including a wall that encloses said passage, and at least one detectable coding element embedded at a selected circumferential position in said wall;

wherein said wall includes at least one hole for receiving said at least one coding element, said at least one coding element being embedded in said hole by an adhesive, and wherein said coding element is recessed in said hole from an exterior surface of said wall, said adhesive being disposed to fill said recess.

34. A method for making a surgical instrument comprising providing a hollow outer member having an opening in a distal region thereof for admitting tissue and having a plastic hub mounted to a proximal region thereof, said plastic hub including a wall that encloses a passage through said hub, defining at least one hole at a selected circumferential position in said wall for receiving at least one detectable coding element, orienting said hole radially with respect to a longitudinal axis of said hub, embedding said at least one coding element in said hole, and disposing an inner member through said passage of said hub for movement within said outer member so that a surgical tool supported by a distal region of said inner member is disposed adjacent to said opening.

35. The method of claim 34 wherein said step of embedding includes providing a friction fit between said coding element and sides of said hole.

36. The method of claim 34 further wherein said step of embedding includes displacing a region of a plastic wall adjacent said hole to lie over at least a portion of said coding element.

37. The method of claim 36 further comprising completely covering said coding element with said region of said plastic wall.

38. The method of claim 34 wherein said step of embedding includes securing a plastic cap over said coding element.

39. The method of claim 34 wherein said step of embedding includes securing said coding element in said hole with an adhesive.

40. A method for making a surgical instrument comprising providing a hollow outer member having an opening in a distal region thereof for admitting tissue and having a plastic hub mounted to a proximal region thereof, said plastic hub including a wall that encloses a passage through said hub, defining at least one hole at a selected circumferential position in said wall for receiving at least one detectable coding element, embedding said at least one coding element in said hole, wherein said step of embedding includes displacing a region of a plastic wall adjacent said hole to lie over at least a portion of said coding element, and disposing an inner member through said passage of said hub for movement within said outer member so that a surgical tool supported by a distal region of said inner member is disposed adjacent to said opening.

41. The method of 40 further comprising completely covering said coding element with said region of said plastic wall.

42. A method for making a surgical instrument comprising providing a hollow outer member having an opening in a distal region thereof for admitting tissue and having a plastic hub mounted to a proximal region thereof, said plastic hub including a wall that encloses a passage through said hub, defining at least one hole at a selected circumferential position in said wall for receiving at least one detectable coding element, embedding said at least one coding element in said hole, wherein said step of embedding includes securing a plastic cap over said coding element, and disposing an inner member through said passage of said hub for movement within said outer member so that a surgical tool supported by a distal region of said inner member is disposed adjacent to said opening.

43. A method for making a surgical instrument comprising providing a hollow outer member having an opening in a distal region thereof for admitting tissue and having a plastic hub mounted to a proximal region thereof, said plastic hub including a wall that encloses a passage through said hub, defining at least one hole at a selected circumferential position in said wall for receiving at least one detectable coding element, embedding said at least one coding element in said hole, wherein said step of embedding includes securing said coding element in said hole with an adhesive, and disposing an inner member through said passage of said hub for movement within said outer member so that a surgical tool supported by a distal region of said inner member is disposed adjacent to said opening.

44. A method for making a surgical instrument comprising providing a hollow outer member having an opening in a distal region thereof for admitting tissue and having a plastic hub mounted to a proximal region thereof, said plastic hub including a wall that encloses a passage through said hub, forming said hub by injection molding, embedding at least one detectable coding element at a selected circumferential position in said wall, wherein said step of embedding includes molding said coding element into said wall during said injection molding of said hub, and disposing an inner member through said passage of said hub for movement within said outer member so that a surgical tool supported by a distal region of said inner member is disposed adjacent to said opening.

45. The method of claim 44 further comprising holding said coding element in said selected circumferential position during at least part of said injection molding of said hub.

46. The method of claim 44 further comprising holding said coding element until said injection molding of said hub is complete, and then releasing said coding element.

47. The method of claim 44 further comprising holding said coding element until a portion of said coding element has been covered by plastic during said injection molding of said hub, then releasing said coding element, and then completing said injection molding of said hub.

* * * * *